(12) United States Patent
Kojima et al.

(10) Patent No.: US 9,433,434 B2
(45) Date of Patent: Sep. 6, 2016

(54) FLUID EJECTION DEVICE AND MEDICAL INSTRUMENT

(71) Applicant: SEIKO EPSON CORPORATION, Tokyo (JP)

(72) Inventors: Hideki Kojima, Matsumoto (JP); Atsuya Hirabayashi, Chino (JP)

(73) Assignee: Seiko Epson Corporation, Tokyo (JP)

( * ) Notice: Subject to any disclaimer, the term of this patent is extended or adjusted under 35 U.S.C. 154(b) by 1 day.

(21) Appl. No.: 14/475,884

(22) Filed: Sep. 3, 2014

(65) Prior Publication Data

US 2014/0371773 A1 Dec. 18, 2014

Related U.S. Application Data

(63) Continuation of application No. 13/269,885, filed on Oct. 10, 2011, now abandoned.

(30) Foreign Application Priority Data

Oct. 12, 2010 (JP) ................................ 2010-229325

(51) Int. Cl.
*A61B 17/3203* (2006.01)
*A61B 17/00* (2006.01)

(52) U.S. Cl.
CPC .. *A61B 17/3203* (2013.01); *A61B 2017/00154* (2013.01); *A61B 2217/005* (2013.01); *A61B 2217/007* (2013.01)

(58) Field of Classification Search
CPC ............. A61B 17/3203; A61B 17/32037; A61B 17/3205; A61B 2017/00154; A61B 2017/32035; A61B 2017/32032; A61B 2017/00225; A61B 2017/00181; A61B 2217/005; A61B 2217/007; A61M 25/0032; A61M 25/0023; A61M 2025/0035; B05B 17/0607

See application file for complete search history.

(56) References Cited

U.S. PATENT DOCUMENTS 3,630,207 A * 12/1971 Kahn .................. A61M 1/3659
604/524
5,114,399 A * 5/1992 Kovalcheck ... A61B 17/320758
604/22

(Continued)

FOREIGN PATENT DOCUMENTS

EP 0-555-549 8/1993
JP 01-146541 6/1989

(Continued)

OTHER PUBLICATIONS

European Search Report for Application No. 11184471.8 dated Apr. 10, 2015.

(Continued)

*Primary Examiner* — Jocelin Tanner
(74) *Attorney, Agent, or Firm* — Workman Nydegger (57) ABSTRACT

A fluid ejection device includes a pulsation generator which converts a fluid into a pulsed fluid, a fluid supply unit (supply pump) which supplies the fluid to the pulsation generator, an ejection tube which has an ejection opening communicating with the pulsation generator, a suction tube into which the ejection tube is inserted with play, a suction channel provided between the suction tube and the ejection tube, a suction opening provided at an end of the suction channel in a vicinity of the ejection opening, and a suction unit (suction pump) which sucks fluid in such a manner that the fluid introduced from the suction opening passes through the suction channel. The ejection opening is held by an inner circumferential part of the suction opening. According to this structure, vibration of the ejection tube in the vicinity of the ejection opening can be reduced.

5 Claims, 4 Drawing Sheets (56) References Cited

U.S. PATENT DOCUMENTS

| | | | |
|---|---|---|---|
| 5,322,504 A * | 6/1994 | Doherty | A61B 17/3203 604/22 |
| 5,529,580 A | 6/1996 | Kusunoki et al. | |
| 5,743,875 A * | 4/1998 | Sirhan | A61L 29/041 604/524 |
| 7,901,374 B2 | 3/2011 | Seto et al. | |
| 2007/0106303 A1* | 5/2007 | Dodick | A61B 17/3421 606/108 |
| 2008/0086077 A1* | 4/2008 | Seto | A61B 17/3203 604/48 |
| 2009/0171271 A1* | 7/2009 | Webster | A61B 17/3417 604/95.01 |
| 2010/0079522 A1 | 4/2010 | Seto et al. | |
| 2011/0089256 A1 | 4/2011 | Kojima | |
| 2011/0137225 A1 | 6/2011 | Feng et al. | |
| 2011/0190804 A1 | 8/2011 | Sekino | |
| 2011/0215170 A1 | 9/2011 | Kojima | |

FOREIGN PATENT DOCUMENTS

| | | |
|---|---|---|
| JP | 01-313047 | 12/1989 |
| JP | 01-314558 | 12/1989 |
| JP | 06-090957 | 4/1994 |
| JP | 2008-082202 | 4/2008 |
| JP | 2011-193949 | 10/2011 |
| JP | 2012-192072 | 10/2012 |

OTHER PUBLICATIONS

U.S. Appl. No. 13/269,885, Mar. 27, 2013, Office Action.
U.S. Appl. No. 13/269,885, Jul. 30, 2013, Final Office Action.
U.S. Appl. No. 13/269,885, Nov. 22, 2013, Office Action.
U.S. Appl. No. 13/269,885, Jun. 10, 2014, Final Office Action.

* cited by examiner

FLUID EJECTION DEVICE AND MEDICAL INSTRUMENT

CROSS-REFERENCE TO RELATED APPLICATIONS

The present application is a Continuation of U.S. patent application Ser. No. 13/269,885, filed on Oct. 10, 2011, which claims priority to Japanese Patent Application No: 2010-229325, filed Oct. 12, 2010, which applications are expressly incorporated by reference herein.

BACKGROUND

1. Technical Field

Embodiments of the present invention relate to a fluid ejection device, and a medical instrument including the fluid ejection device.

2. Related Art

A fluid ejection device capable of excising, incising, and crushing living tissue has excellent characteristics when used as a surgical instrument. A low probability of heat damage and preservation of blood vessels including capillaries are examples of these characteristics.

During surgery, a surgery target may become obscured from view while using the fluid ejection device. A certain type of fluid ejection device has a suction tube which sucks and removes the ejected liquid, excised tissue or the like remaining on the surgery target so as to ensure that the surgery target remains visible during surgery.

This type of fluid ejection device includes an ejection tube through which high-pressure fluid is ejected. The ejection tube is disposed within a suction channel of a suction tube in such a position so as to be concentric with the suction channel (for example, see JP-A-1-313047).

Another example of the fluid ejection device has an ejection tube through which high-pressure fluid is ejected. This ejection tube is inserted into a suction tube eccentrically with respect to the inner circumferential surface of the suction tube (for example, see JP-A-6-90957).

A further example of the fluid ejection device is equipped with a volume varying unit which rapidly varies the volume of a fluid chamber so as to convert the fluid into a pulsed fluid. The fluid is thus ejected in pulses at high speed through an ejection opening (for example, see JP-A-2008-82202).

According to the fluid ejection devices disclosed in JP-A-1-313047 and JP-A-6-90957, however, the ejection tube vibrates when fluid is ejected in pulses at high speed when using the technology disclosed in JP-A-2008-82202. More specifically, the ejection tube provided within the suction tube is not supported or fixed except at the root of the ejection tube. As a result, vibrations occur at the tip of the ejection tube when fluid is ejected in pulses at high speed. Several problems arise from the vibrations that occur at the tip of the ejection tube. For example, there is a decrease in the positional accuracy of the fluid ejection. In addition, vibration noise is generated by the interference between the ejection tube and the suction tube into which the ejection tube is inserted.

To overcome these problems, a structure has been adopted which includes a support member within the suction tube to firmly support the ejection tube. However, this structure is complicated. In addition, this structure deteriorates the maneuverability of the fluid ejection device due to the increased size and weight of the fluid ejection device resulting from this structure.

SUMMARY

An advantage of some aspects of embodiments the invention is to solve at least a part of the aforementioned problems. Embodiments of the invention can be implemented according to the following forms or application examples.

Application Example 1

This application example is directed to a fluid ejection device including: a pulsation generator which converts fluid into a pulsed fluid; a fluid supply unit which supplies the fluid to the pulsation generator; an ejection tube which has an ejection opening communicating with the pulsation generator; a suction tube into which the ejection tube is inserted with play; a suction channel provided between the inner circumferential surface of the suction tube and the outer circumferential surface of the ejection tube; a suction opening provided at the end of the suction channel in the vicinity of the ejection opening; and a suction unit which sucks the fluid in such a manner that the fluid introduced from the suction opening passes through the suction channel. The ejection opening is held by an inner circumferential part of the suction opening.

According to this application example of the invention, the ejection opening of the ejection tube is held by the inner circumferential part of the suction tube. In this case, the tip of the ejection tube does not easily vibrate during high-speed ejection of pulsed fluid. In the case of the fluid ejection device which has the ejection tube inserted into the suction tube with play provided therebetween (e.g., between the ejection tube and the suction tube), both an increase in the positional accuracy of the fluid ejection and a reduction of abnormal noise can be achieved by a simple structure without increasing the size and weight of the fluid ejection device.

Application Example 2

This application example of the invention is directed to the fluid ejection device of the above application example. In this application example, across-sectional shape of the suction opening in the direction perpendicular to the extending direction of the suction tube is a flat shape.

According to this application example of the invention, the cross-sectional shape of the suction opening has a flat shape or a flattened shape. In one example, the cross-sectional shape of the suction opening or the tip of the suction tube may be flatter than another portion of the suction tube. In this case, the suction opening can be sufficiently opened under the condition in which the ejection tube is held by the inner circumferential surface of the suction tube. The flat shape of the suction opening, for example, may be expanded upon insertion of the ejection tube, which sufficiently opens the suction opening for sucking. Moreover, the suction tube having the flat portion in the vicinity of the suction opening (tip portion of the ejection tube) can be easily inserted into a narrow surgery target portion, which further improves the maneuverability of the fluid ejection device.

Application Example 3

This application example of the invention is directed to the fluid ejection device of the above application example. In this application example, across-sectional shape of the suction opening in the direction perpendicular to the extending direction of the suction tube is a substantially elliptic shape.

According to this application example of the invention, the cross-sectional shape of the suction opening has a substantially elliptic shape. In this case, a sufficient opening area of the suction opening can be produced. The portion corresponding to the major axis of the elliptic shape of the suction opening under the condition in which the ejection tube is held by the portion of the suction opening corresponding to the minor axis of the elliptic shape of the suction opening provides the opening area. Moreover, the suction tube having a flat shape formed by the elliptic shape in the vicinity of the suction opening can be easily inserted into a narrow surgery target portion, which further improves the maneuverability of the fluid ejection device. Furthermore, the suction opening having the substantially elliptic shape is not easily caught by the surgery target portion. Even when the suction opening contacts the surgery target portion, the surgery target portion is not damaged thereby.

Application Example 4

This application example of the invention is directed to the fluid ejection device of the above application example. In this application example, the ejection opening is positioned substantially at a center of the suction opening.

According to this application example of the invention, the ejection opening is positioned substantially at the center of the major axis of the suction tube. Thus, the position of the ejection opening is easily recognized, which facilitates ejection of the fluid toward the surgery target portion.

Application Example 5

This application example of the invention is directed to the fluid ejection device of the above application example. In this application example, the tip of the suction tube including the suction opening engages with the suction tube in such a manner so as to be rotatable around the axis of the suction tube.

According to this application example of the invention, the tip of the suction tube is rotatable around the axis of the suction tube. In this case, the direction of the tip of the suction tube can be controlled in accordance with the shape of the surgery target portion. Thus, the maneuverability of the fluid ejection device further improves.

Application Example 6

This application example of the invention is directed to a medical instrument including the fluid ejection device of the above application example of the invention.

A medical instrument including the fluid ejection device of the above application example of the invention can effectively provide excellent characteristics of a surgery instrument.

BRIEF DESCRIPTION OF THE DRAWINGS

Embodiments of the invention will be described with reference to the accompanying drawings, wherein like numbers reference like elements.

DESCRIPTION OF EXEMPLARY EMBODIMENT

Embodiments according to the invention are hereinafter described with reference to the drawings. Scales different from the actual ones are set for components and parts shown in the respective figures so that these components and parts can be expanded to sufficient sizes easily recognizable in the figures.

First Embodiment

Figure 1:
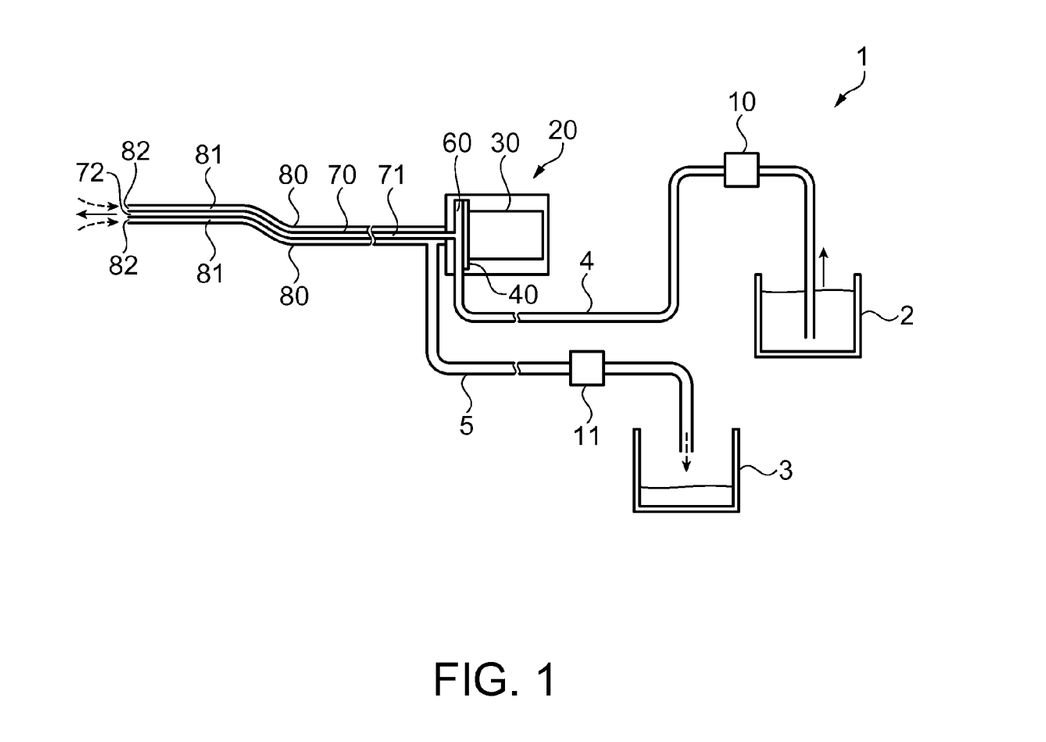
FIG. 1 illustrates a structure of a fluid ejection device according to a first embodiment.

FIG. 1 illustrates a structure of a fluid ejection device according to a first embodiment. In this embodiment, a fluid ejection device included in a medical instrument will be discussed. The fluid ejection device in this embodiment includes, but is not limited to, functions such as excision, incision, exfoliation, and crushing. Further, the fluid ejection device is not limited to applications in the medical field.

As illustrated in FIG. 1, a fluid ejection device 1 includes a fluid supply container 2 storing fluid, a supply pump 10 as a fluid supply unit, a pulsation generator 20 which converts fluid supplied from the supply pump 10 into pulsed fluid, an ejection tube 70 which communicates with the pulsation generator 20, a suction tube 80 which extends from the pulsation generator 20, a suction pump 11 as a suction unit, and a waste fluid container 3 which stores sucked waste liquid and excised tissue. The pulsation generator 20, the supply pump 10, and the fluid supply container 2 are connected with one another via a fluid supply channel tube 4. The suction tube 80, the suction pump 11, and the waste fluid container 3 are connected with one another via a suction channel tube 5.

The pulsation generator 20 may be constituted by any type of generator that can eject fluid in pulses. Examples include a piezoelectric type and a bubble jet type. In this embodiment, the pulsation generator 20 includes a piezoelectric type generator. Fluid used herein may be physiological salt water as an example, although other fluids are within the scope of the disclosure. The ejection tube 70 includes an ejection channel 71 communicating with a fluid chamber 60 formed within the pulsation generator 20, and an ejection opening 72 disposed at a tip of the ejection tube 70. The ejection opening 72 may be configured as an opening having a reduced flow channel width.

The ejection tube 70 is inserted into the suction tube 80 with play provided therebetween. The ejection tube 70 may be held by a part of the inner circumferential surface of the suction tube 80 in the vicinity of the ejection opening 72. The space formed between the inner circumferential surface of the suction tube 80 and the outer circumferential surface of the ejection tube 70 corresponds to or defines a suction channel 81. A suction opening 82 is provided at the end of the suction channel 81 in the vicinity of the ejection opening 72. In one example, the ejection tube 70 is rigid enough to not be deformed by fluid pressure produced at the time of fluid ejection. The suction tube 80 is rigid enough to not be deformed by negative pressure produced by the suction pump 11.

The flow of fluid produced by the fluid ejection device 1 as constructed is now briefly explained. Fluid stored in the fluid supply container 2 is sucked by the supply pump 10, and supplied to the pulsation generator 20 via the fluid supply channel tube 4 at constant pressure in one embodiment.

The pulsation generator 20 includes the fluid chamber 60, a piezoelectric device 30 as a volume varying unit which varies the volume of the fluid chamber 60, and a diaphragm 40. The pulsation generator 20 actuates the piezoelectric device 30 to generate a pulsed flow within the fluid chamber 60. This pulsed flow passes through the ejection channel 71, and comes out of the ejection opening 72 as a high-speed ejection flow in pulses.

When the pulsation generator 20 stops operation, that is, does not change the volume of the fluid chamber 60, the fluid supplied from the supply pump 10 at constant pressure passes through the fluid chamber 60 and comes out of the ejection opening 72 as a continuous ejection flow.

The pulsed flow of fluid herein refers to a flow of fluid whose flow direction is kept constant or substantially constant and whose flow amount or flow speed changes periodically or irregularly. The pulsed flow includes an intermittent flow that repeatedly flows and stops. However, the pulsed flow may include other types of flow as long as the flow amount or flow speed of fluid changes periodically or irregularly.

Similarly, the ejection of fluid in pulses refers to the ejection of fluid whose flow amount or moving speed varies periodically or irregularly. The ejection of fluid in pulses includes an intermittent ejection which repeats the ejection and non-ejection of fluid, for example. However, the ejection in pulses may include other types of ejection as long as the flow amount or moving speed of fluid to be ejected changes periodically or irregularly.

The suction mechanism is now explained. The fluid ejected from the ejection opening 72 remains on the surgery target portion as waste liquid. Moreover, excised living tissue (hereinafter abbreviated as excised tissue) stays on the surgery target portion as well. The waste liquid and excised tissue are sucked by the suction pump 11 through the suction opening 82, and passed though the suction channel 81 and the suction channel tube 5 to be stored in the waste fluid container 3. The operation of the suction pump 11 may be initiated in correlation with the operation of the pulsation generator 20. Alternatively, the suction pump 11 may be intermittently operated at regular intervals, or only operated as necessary.

There are several shapes and structures of the ejection tube 70 and the suction tube 80 considered as appropriate examples. The details of these shapes and structures are hereinafter described as specific examples in conjunction with the associated drawings.

First Example

Figure 2A:
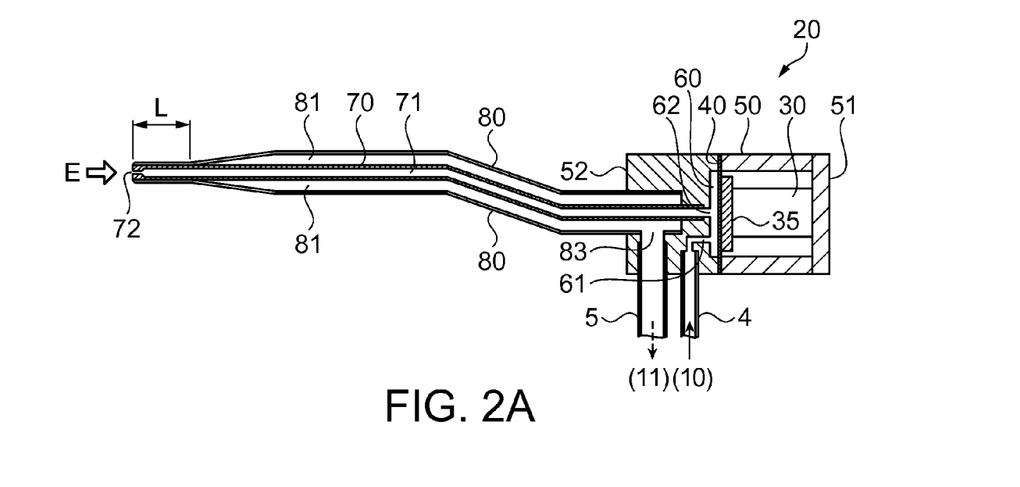
FIG. 2A is a side cross-sectional view showing example structures of a pulsation generator, an ejection tube, and a suction tube according to a first example.
Figure 2B:
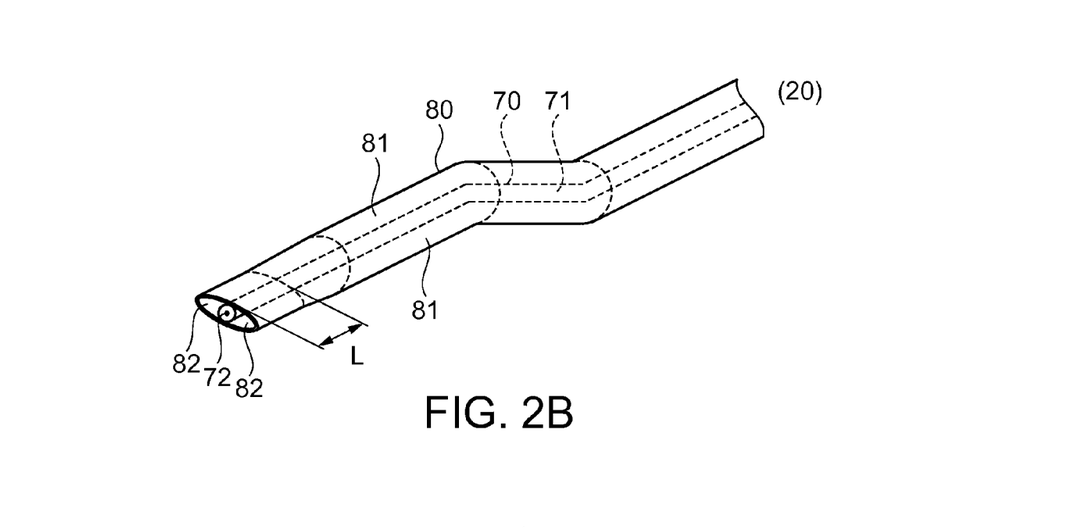
FIG. 2B is a perspective view showing an example of the tip structure of the ejection tube and the suction tube.
Figure 2C:
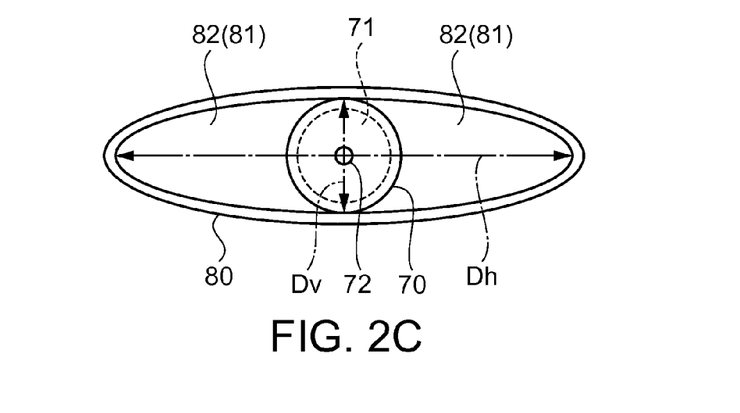
FIG. 2C is a front view showing examples of the tips of the ejection tube and the suction tube as viewed from the tip side (E direction in FIG. 2A).

FIG. 2A is a side cross-sectional view of the pulsation generator, the ejection tube, and the suction tube according to the first example taken along a plane extending in the flow direction of the fluid. FIG. 2B is a perspective view illustrating a tip structure of the ejection tube and the suction tube. FIG. 2C is a front view illustrating example tips of the ejection tube and the suction tube as viewed from the tip direction (direction of E in FIG. 2A).

As illustrated in FIG. 2A, the pulsation generator 20 includes an inlet channel 61 through which fluid supplied from the supply pump 10 via the fluid supply channel tube 4 is introduced into the fluid chamber 60. The pulsation generator 20 also includes the piezoelectric device 30 and the diaphragm 40 as the volume varying unit for varying the volume of the fluid chamber 60, and an outlet channel 62 communicating with the fluid chamber 60.

The diaphragm 40 is formed by a disk-shaped metal thin plate in this example, and is fixed by close contact with a lower case 50 and an upper case 52. The piezoelectric device 30 is a laminated piezoelectric device in this example. One of the ends of the piezoelectric device 30 is fixed to the diaphragm 40 via an upper plate 35, while the other end of the piezoelectric device 30 is fixed to a bottom plate 51.

The liquid chamber 60 is a space produced between the diaphragm 40 and a recess formed on the surface of the upper case 52 opposed to the diaphragm 40. The outlet channel 62 is opened substantially at the center of the fluid chamber 60 in this example.

The upper case 52 and the lower case 50 are joined to each other via the opposed faces thereof to be formed into one body (in the example shown in FIG. 2A, the diaphragm 40 is interposed between the cases 52 and 50). The ejection tube 70 may be inserted into the upper case 52 by press-fit. The ejection tube 70 includes the ejection channel 71 which communicates with the outlet channel 62. The ejection opening 72 may have a reduced channel diameter and is opened at the tip of the ejection tube 70. The ejection opening 72 may be provided as a nozzle.

The suction tube 80 provided as a jacket tube of the ejection tube 70 extends from the upper case 52. An opening 83 is formed in the vicinity of the root end of the suction tube 80 on the side close to the pulsation generator 20 in such a manner as to penetrate the tube wall of the suction tube 80. The suction channel tube 5 attached to the opening 83 communicates with the opening 83.

According to this structure, the extending direction of the suction channel tube 5 in the vicinity of the pulsation generator 20 is equalized with the direction of the fluid supply channel tube 4. In this case, the maneuverability of the fluid ejection device 1 improves when the ejection device 1 is used by an operator (operator of the ejection device) who holds the pulsation generator 20 during operation of the fluid ejection device 1. The ejection tube 70 and the suction tube 80 may be tubes extending in straight lines. However, the tubes 70 and 80 may be bent as illustrated in FIG. 2A so that visibility around the ejection opening 72 can be secured without the hand and fingers of the operator holding the fluid ejection device 1 impeding visibility around the ejection opening 72.

As illustrated in FIGS. 2B and 2C, the tip of the ejection tube 70 in the vicinity of the ejection opening 72 is held by a flat part of the inner circumferential surface of the suction tube 80. More specifically, the cross section of a holding area L of the suction tube 80 in the vicinity of the suction opening 82 has a substantially elliptic shape having a major axis Dh and a minor axis Dv such that two points of the ejection tube 70 opposed to each other approximately in the direction of the diameter can be held by the part of the suction tube 80 corresponding to the position of the minor axis Dv.

While the suction tube 80 has a flat shape produced by the substantially elliptic cross section in this example, the direction of flatness is not limited to this direction. For example, the suction tube 80 may have a substantially elliptic shape which has the major axis Dv and the minor axis Dh. In addition, while only the tip portion of the suction tube 80 has the substantially elliptic shape in this example, the entire shape as well as the tip portion of the suction tube 80 may be substantially elliptic when at least the part of the ejection tube in the vicinity of the ejection opening is held by the inner circumferential part of the suction tube.

The suction channel 81 and the suction opening 82 are formed by the space between the outer circumference of the ejection tube 70 and the inner circumference of the suction tube 80. In this case, as illustrated in FIGS. 2B and 2C, the space corresponding to the suction channel 81 and the suction opening 82 in the holding area L becomes wider as the major axis Dh of the substantially elliptic cylindrical shape of the suction tube 80 increases. When the two points of the ejection tube 70 opposed to each other approximately in the direction of the diameter are held by the part of the suction tube 80 corresponding to the position of the minor axis Dv, substantially the same opening area is produced in the suction opening 82 on each side of the ejection opening 72. In other words, the ejection opening 72 is positioned substantially at the center of the major axis Dh in one example.

The ejection tube 70 can be fixed to the suction tube 80 by applying an adhesive, a solder or other fixing materials to the portion of the inner circumference of the suction tube 80 holding the outer circumference of the ejection tube 70. Alternatively, the ejection tube 70 may be held and fixed by pressing and deforming the portion of the suction tube 80 corresponding to the holding area L such that this portion becomes a flat portion after the ejection tube 70 is inserted into the suction tube 80 with play provided between the ejection tube 70 and the suction tube 80. The length of the holding area L may be arbitrarily determined as long as the ejection tube 70 can be securely held and fixed by the length of the holding area L. Thus, the holding area L may be provided only at the tip of the ejection tube 70.

According to the fluid ejection device in this example, the following advantages can be offered.

The area of the ejection tube 70 in the vicinity of the ejection opening 72 can be easily held and fixed without using an additional support member provided within the suction tube 80. According to this structure, at least two points of the ejection tube 70 opposed to each other in the direction of the diameter can be held by the suction tube 80, in which condition the ejection tube 70 can be more firmly fixed.

Since the area of the ejection tube 70 around the ejection opening 72 is held by the suction tube 80 in one example, vibration at the tip of the ejection tube 70 can be reduced during a high-speed ejection of a pulsed flow. Thus, even in the case of the fluid ejection device having the structure in which the ejection tube 70 is inserted into the suction tube 80 with play provided therebetween, a high-speed ejection of fluid in pulses toward the surgery target position can be accurately achieved. Moreover, in the condition where the outer circumference of the ejection tube 70 is directly held by the inner circumference of the suction tube 80, abnormal noise, which might be generated due to vibration by the contact between the ejection tube 70 and the suction tube 80, is not generated.

The cross section of the portion of the suction tube 80 corresponding to the holding area L has a substantially elliptic shape in one example. Thus, when the major axis Dh of the suction tube 80 is long, the suction tube 80 obtains a sufficient opening area of the suction opening 82 while holding and fixing the ejection tube 70. In other words, the suction opening 82 of the suction tube 80 is sufficiently open to enable suction.

The portion of the suction tube 80 in the holding area L has the flat shape corresponding to the elliptic cross-sectional shape. In this case, the fluid ejection device 1 can be easily inserted into a narrow surgery target portion such as an incision target and an exfoliation target. Thus, the maneuverability of the fluid ejection device 1 during surgery is further improved.

The ejection opening 72 is disposed substantially at the center of the major axis Dh of the suction tube 80. Accordingly, the operator can easily recognize the position of the ejection opening 72 and can easily operate the fluid ejection device 1 to eject fluid toward the surgery target.

According to this example, therefore, vibration of the ejection tube 70 and abnormal noise generated thereby can be reduced by a simple structure without increasing the size and weight of the fluid ejection device 1. Further, fluid can be accurately ejected from the fluid ejection device 1 toward an accurate target position. The maneuverability of the fluid ejection device 1 is improved.

Second Example

Figure 3A:
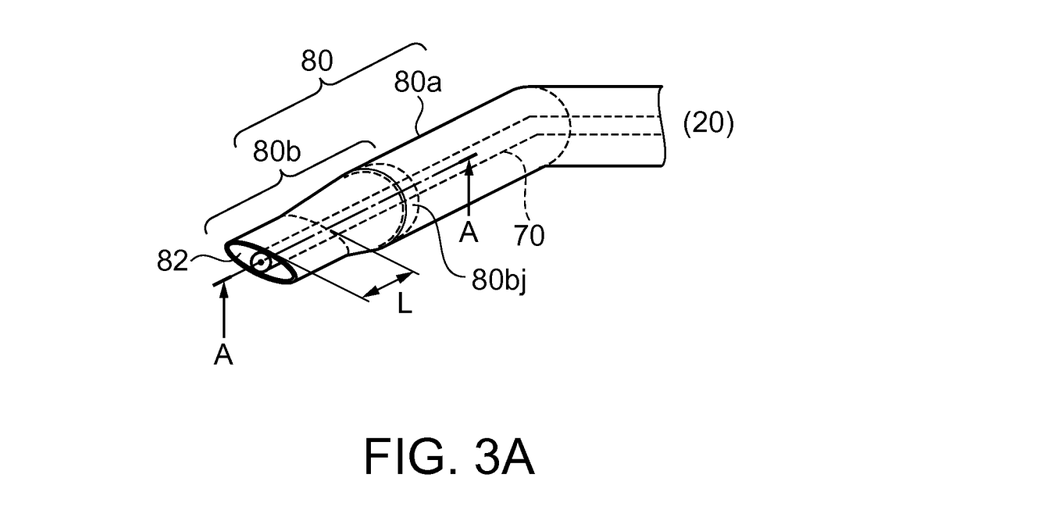
FIG. 3A is a perspective view showing an example of a tip structure of an ejection tube and a suction tube according to a second example.
Figure 3B:
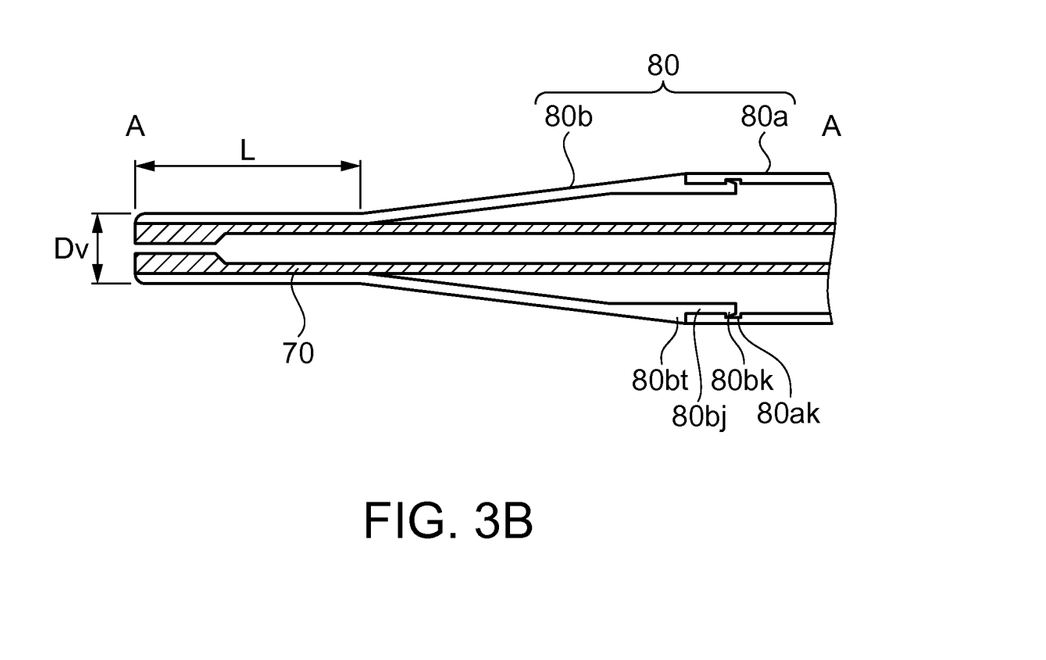
FIG. 3B is a cross-sectional view taken along a line A-A in FIG. 3A.

A second example is now described with reference to the drawings. FIG. 3A is a perspective view illustrating an example of a tip structure of the ejection tube and the suction tube according to the second example. FIG. 3B is a cross-sectional view taken along a line A-A in FIG. 3A. According to the first example, the suction tube 80 is constituted by a single piece structure. In this example, however, the tip portion of the suction tube 80 is a component that can be separated from the suction tube 80 and that engages with the suction tube 80 in such a manner as to be rotatable around the axis of the suction tube 80. Components and parts in this example which correspond to similar components and parts in the first example have been given similar reference numbers, and the same explanation is not repeated.

As illustrated in FIG. 3A, the suction tube 80 has a tip portion 80b, and a suction tube portion 80a extending between the pulsation generator 20 and the tip portion 80b. The tip portion 80b engages with the suction tube portion 80a.

The tip portion 80b includes the area corresponding to the holding area L, and a joint 80bj which can be inserted into the suction tube 80a for engagement therewith and sliding thereon in such a manner as to be rotatable. The tip portion 80b also includes an engaging portion provided between the holding area L and the joint 80bj. In the engaging portion, the minor axis Dv of the substantially elliptic cylinder gradually increases to produce a substantially circular shape.

The joint 80bj is a cylindrical component constituting an engaging portion between the tip portion 80b and the suction tube portion 80a. The joint 80bj extends from the end of the tip portion 80b on the side contacting the suction tube portion 80a. The outer circumference of the joint 80bj contacts the inner circumference of the engaging area of the suction tube portion 80a and slides thereon in such a manner as to be rotatable. The tip portion 80b can be rotated with respect to the suction tube portion 80a. Stoppers 80bt and 80bk are provided on the extended portion of the joint 80bj. The stopper 80bt is a part for preventing the tip portion 80b from being excessively inserted into the suction tube portion

80*a* by the negative pressure produced by the suction pump 11. The stopper 80*bk* is a part for preventing separation of the tip portion 80*b* from the engagement with the suction tube portion 80*a*. A notch 80*ak* corresponding to the shape of the stopper 80*bk* is provided on the suction tube portion 80*a*. When the tip portion 80*b* is inserted in the suction tube portion 80*a*, the notch 80*ak* engages with the stopper 80*bk*.

The outer circumference of the joint 80*bj* slides on the inner circumference of the suction tube portion 80*a*, and the area of the outer circumference of the ejection tube 70 corresponding to the holding area L slides on the inner circumference of the tip portion 80*b*. As a result, the tip portion 80*b* can rotate with respect to the suction tube portion 80*a* around the axis thereof. According to the first example, a fixing material such as an adhesive and a solder is applied to the portion where the outer circumference of the ejection tube 70 is held by the inner circumference of the suction tube 80. In this example, however, such a fixing material is not applied to this area to allow sliding and/or rotation of the tubes 70 and 80 relative to each other. The tip portion 80*b* can slide in at least a rotational motion. The fluid ejection device in this example can provide at least the following advantages. According to this structure, the tip portion 80*b* is rotatable with respect to the suction tube portion 80*a* around the axis thereof.

In one example, the operator can control the direction of the suction opening in accordance with the shape of the surgery target portion. More specifically, the direction of the tip portion 80*b* having a flat shape can be varied (e.g., by rotating the tip portion 80*b*) according to the shape of a narrow surgery target portion such as an incision target, or changed in such a direction that the surgery target portion can be easily seen.

Accordingly, the fluid ejection device in this example can offer an advantage of further improvement over the maneuverability of the fluid ejection device as well as the advantages provided in the first example.

Third Example

Figure 4A:
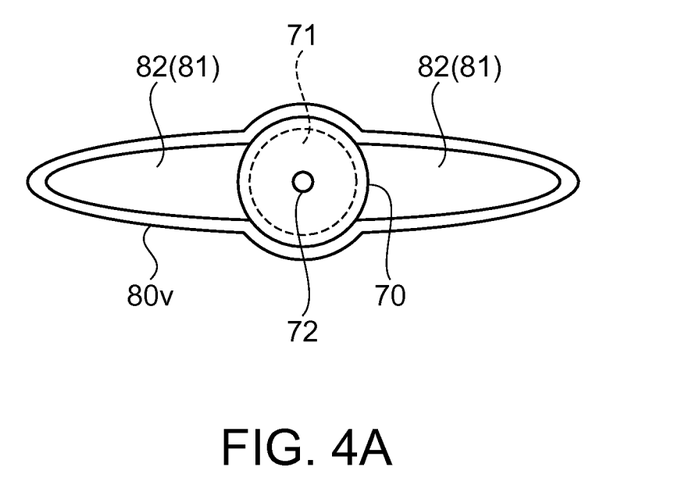
FIG. 4A is a front view showing examples of tips of an ejection tube and a suction tube as viewed from the tip side according to a third example.

A third example is now described with reference to the drawings. FIG. 4A is a front view of example tips of the ejection tube and the suction tube according to the third example as viewed from the tip side (direction of E in FIG. 2A). According to the first and second examples, the suction tube 80 has a substantially elliptic cross section in the holding area L (FIG. 2C). However, the cross section in each of the tips may have a shape of a suction tube 80*v* shown in FIG. 4A. Components and parts in this example which correspond to similar components and parts in the above examples have been given similar reference numbers, and the same explanation is not repeated.

The suction tube 80*v* has a flat shape produced by further pressing the suction tube 80 having the substantially elliptic shape in the first and second examples against the ejection tube 70. The suction tube 80*v* holds the ejection tube 70 via the surface of the suction tube 80*v* extending almost along the curvature of the outer circumference of the ejection tube 70. In this example, approximately half the area of the outer circumferential surface of the ejection tube 70 in the holding portion (holding area L) is held by the inner circumference of the suction tube 80*v*.

According to this example, therefore, the suction tube 80*v* can more firmly hold the ejection tube 70. The suction tube 80*v* is pressed flat to shape a portion of the suction tube 80*v* against more of the outer circumferential surface of the ejection tube 70 than previous examples. The suction tube 80*v* thus follows the shape of the ejection tube 70. Moreover, the suction tube 80*v* has a more flat shape and can be easily inserted into a narrower surgery target portion such as an incision target or an exfoliation target, which improves the maneuverability of the fluid ejection device during surgery.

Fourth Example

Figure 4B:
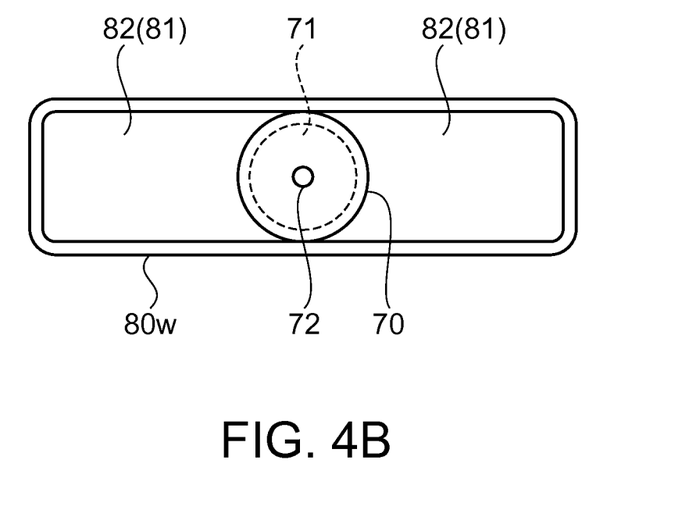
FIG. 4B is a front view showing examples of tips of an ejection tube and a suction tube as viewed from the tip side according to a fourth example.

A fourth example is now described with reference to the drawings. FIG. 4B is a front view of example tips of the ejection tube and the suction tube according to the fourth example as viewed from the tip side. The cross-sectional shape of the suction tube 80 in the holding area L according to each of the first and second examples may have a shape of a suction tube 80*w* shown in FIG. 4B. Components and parts in this example which correspond to similar components and parts in the above examples have been given similar reference numbers, and the same explanation is not repeated.

The tip of the ejection tube 70 in the vicinity of the ejection opening 72 is held by the inner circumference of the suction tube 80*w* having a flat shape. More specifically, the cross section of the suction tube 80*w* in the holding area L has a substantially rectangular shape in this example. The length of the short side of the rectangular shape is substantially equivalent to the outside diameter of the ejection tube 70 being held. The centers of the two long sides of the suction tube 80*w* substantially hold two points of the ejection tube 70 opposed to each other in the direction of the diameter. Each of the four corners of the cross section of the substantially rectangular shape has a round shape for protecting the surgery target in contact with the suction tube 80*w* in one example.

According to this example, the width of the suction tube 80*w* in the vicinity of the suction opening 82 is equivalent to each of the corresponding widths of the suction tube 80 (FIG. 2C) and the suction tube 80*v* (FIG. 4A). However, the opening area of the suction opening 82 becomes wider due to the rectangular cross section. Thus, the fluid and the excised tissue can be further efficiently sucked and removed through the suction tube.

Medical Instrument

A medical instrument including the fluid ejection device 1 described herein can more effectively provide excellent characteristics of a surgery instrument. More specifically, the fluid ejection device 1 has excellent characteristics as a surgery instrument including low probabilities of heat damage and preservation of blood vessels including capillaries at the time of excision, incision, crush and the like of living tissue. Both the pulsed flow ejection which allows execution of surgery by using a small amount of physiological salt water, and the provision of the suction tube 80 around the ejection tube 70 can help prevent the fluid and excised tissue from blocking the vision of an operator of the fluid ejection device, thereby securing visibility for surgery. The position of the ejection tube 70 substantially at the center of the suction tube 80 allows the operator to easily recognize the position of the ejection opening 72 and allows the operator to easily eject fluid toward the surgery target accurately. The tip portion of the ejection opening 72 under the held and fixed condition does not vibrate during high-speed fluid ejection in pulses, which permits the high-speed pulsed fluid ejection to be directed toward the position of the surgery target with accuracy. Moreover, elimination of abnormal noise generated with vibration allows the operator to concentrate his or her attention further on the surgery.

What is claimed is:

1. A medical instrument comprising:
a pulsation generator for converting a fluid into a pulsed fluid including:
a fluid chamber accommodating the fluid; and
a pressure generator for applying pressure to a fluid within the fluid chamber and converting the fluid into a pulsed fluid flow;
an ejection tube that includes an opening communicating with the pulsation generator;
a suction tube into which the ejection tube is movably inserted;
an upper case and a lower case that form a body for accommodating at least the fluid chamber and the pressure generator, wherein the ejection tube extends from an outlet channel of the pulsation generator and the suction tube extends towards the body;
wherein the ejection tube is held by an inner circumferential surface of the suction tube, the suction tube has a cross sectional area in a crossing direction to an extending direction of the suction tube and the cross sectional area of the suction tube, including an inner lumen thereof, has a major axis and a minor axis; and
the ejection opening is held by a portion of the suction tube corresponding to the minor axis, the portion of the suction tube corresponding to the minor axis comprising a substantially flat, elliptical shape, the suction tube transitioning along its length, from a tip of the suction tube towards the body, from the substantially flat, elliptical shape to another cross-sectional configuration.

2. The medical instrument according to claim 1, wherein the suction opening has a cross sectional area in the crossing direction to the extending direction of a suction tube, and the cross sectional area is a substantially elliptic shape.

3. The medical instrument according to claim 1, wherein the suction tube has another cross sectional area in the crossing direction to the extending direction of the suction tube other than a suction opening, and the cross sectional area is a substantially elliptic shape.

4. The medical instrument according to claim 1, wherein the tip of the suction tube is configured to rotatably engage with the suction tube so that the suction tube is allowed to rotate around its axis.

5. The medical instrument according to claim 1, wherein the medical instrument is for ejecting a pulsed fluid and for incising a biological tissue.

* * * * *